ns2122872, XP008177332

United States Patent
Sedel

(10) Patent No.: US 10,357,480 B2
(45) Date of Patent: Jul. 23, 2019

(54) BIOTIN FOR TREATING PERIPHERAL DEMYELINATING NEUROPATHY

(71) Applicant: MedDay Pharmaceuticals, Paris (FR)

(72) Inventor: Frédéric Sedel, Paris (FR)

(73) Assignee: MEDDAY PHARMACEUTICALS, Paris (FR)

( * ) Notice: Subject to any disclaimer, the term of this patent is extended or adjusted under 35 U.S.C. 154(b) by 0 days.

(21) Appl. No.: 15/561,911

(22) PCT Filed: Mar. 25, 2016

(86) PCT No.: PCT/EP2016/056696
§ 371 (c)(1),
(2) Date: Sep. 26, 2017

(87) PCT Pub. No.: WO2016/151132
PCT Pub. Date: Sep. 29, 2016

(65) Prior Publication Data
US 2018/0125825 A1  May 10, 2018

(30) Foreign Application Priority Data

Mar. 26, 2015  (EP) .................................. 15305437

(51) Int. Cl.
| | | |
|---|---|---|
| A61P 25/28 | (2006.01) |
| A61K 45/06 | (2006.01) |
| A61K 31/4188 | (2006.01) |
| A61P 21/00 | (2006.01) |
| A61K 9/00 | (2006.01) |

(52) U.S. Cl.
CPC ........ *A61K 31/4188* (2013.01); *A61K 9/0019* (2013.01); *A61K 9/0053* (2013.01); *A61K 45/06* (2013.01); *A61P 21/00* (2018.01); *A61P 25/28* (2018.01)

(58) Field of Classification Search
None
See application file for complete search history.

(56) References Cited

U.S. PATENT DOCUMENTS

| | | |
|---|---|---|
| 5,885,976 A | 3/1999 | Sandyk |
| 2005/0249823 A1 | 11/2005 | Murphy et al. |

FOREIGN PATENT DOCUMENTS

| | | |
|---|---|---|
| FR | 2 905 868 A1 | 3/2008 |

OTHER PUBLICATIONS

International Search Report and Written Opinion, issued in PCT/EP2016/056696 dated Aug. 9, 2016, 22 pages.
Daniel B. Drachman et al., "Strategy for Treating Motor Neuron Diseases Using a Fusion Protein of Botulinum Toxin Binding Domain and Streptavidin for Viral Vector Access: Work in Progress," Toxins, 2, 2872-2889; doi: 10.3390/toxins2122872, XP008177332 (2010).
Yanling Yang et al., "Spinal Cord Demyelination Associated With Biotinidase Deficiency in 3 Chinese Patients," Journal of Child Neurology, vol. 22, No. 2, pp. 156-160, XP008126453 (Feb. 1, 2007).
Ayman Tourbah, "Biotin and demyelinating diseases—a new connection?," Multiple Sclerosis Journal, vol. 88, No. 1, pp. 9-19, XP55275784 (Jan. 1, 2000).
Laure Peyro Saint Paul et al., "Pharmacokinetics and pharmacodynamics of MD1003 (high-dose biotin) in the treatment of progressive multiple sclerosis," Expert Opinion on Drug Metabolism & Toxicology, vol. 12, No. 3, XP55275654, pp. 327-344 (2016).
S. Grunewald et al., "Biotinidase Deficiency: a Treatable Leukoencephalopathy," Neuropedlatrlcs, vol. 35, No. 4, pp. 211-216, XP008176768 (Aug. 1, 2004).
Sarbani Raha et al., "Biotinidase Deficiency Presenting as Recurrent Myelopathy in a 7-Year-Old Boy and a Review of the Literature," Pediatric Neurology, vol. 45, No. 4, pp. 261-264, XP028286593 (Jun. 9, 2011).
Kirit Pindolia et al., "Neurological deficits in mice with profound biotinidase deficiency are associated with demyelination and axonal degeneration," Neurobiology of Disease, vol. 47, No. 3, pp. 428-435, XP028399238 (Apr. 29, 2012).
Eman S Al Jumah et al., "Spinal Cord Demyelination in Biotinidase Deficiency: A Case Report," Kuwait Medical Journal, vol. 44, No. 2, pp. 135-138, XP008180400 (Jun. 2, 2012).
Laure Bottin et al., "Biotinidase deficiency mimicking neuromyelitis optica: Initially exhibiting symptoms in adulthood," Multiple Sclerosis Journal, vol. 21, No. 12, pp. 1604-1607, XP008180397 (Oct. 1, 2015).
Shahram Attarian et al., "An exploratory randomised double-blind and placebo-controlled phase 2 study of a combination of baclofen, naltrexone and sorbitol (PXT3003) in patients with Charcot-Marie-Tooth disease type 1A," Orphanet Journal of Rare Diseases, 9:199, 15 pages (2014).
A. F. Hahn et al., "Intravenous immunoglobulin treatment in chronic inflammatory demyelinating polyneuropathy, A double-blind, placebo-controlled, cross-over study," Brain, 119, pp. 1067-1077 (1996).
S Kuwabara, et al., "Long term prognosis of chronic inflammatory demyelinating polyneuropathy: a five year follow up of 38 case," J Neurol Neurosurg Psychiatry, 77:66-70 (2006).
Jean-Marc Leger et al., "Placebo-controlled trial of rituximab in IgM anti-myelin—associated glycoprotein neuropathy," American Academy of Neurology, 80, pp. 2217-2225 (Jun. 11, 2013).
Hiroshi Mitsumoto et al., "ALS Multicenter Cohort Study of Oxidative Stress (ALS COSMOS): The study methodology, recruitment, and baseline demographic and disease characteristics," Amyotroph Lateral Scler Frontotemporal Degener, 15(0): 192-203 (2013).
M Vermeulen et al., "Intravenous immunoglobulin treatment in patients with chronic inflammatory demyelinating polyneuropathy: a double blind, placebo controlled study," J Neurol Neurosurg Psychiatry, 56:36-39 (1993).

*Primary Examiner* — John D Ulm
(74) *Attorney, Agent, or Firm* — Rothwell, Figg, Ernst & Manbeck, p.c.

(57) ABSTRACT

The invention relates to the use of biotin for treating Amyotrophic Lateral Sclerosis, as well as demyelinating peripheral neuropathies and Neuromyelitis optica (NMO).

14 Claims, No Drawings

BIOTIN FOR TREATING PERIPHERAL DEMYELINATING NEUROPATHY

This application is a National Phase of International Application Serial No. PCT/EP2016/056696, filed Mar. 25, 2016, which claims priority of European Application No. 15305437.4, filed on Mar. 26, 2015, which are incorporated herein by reference in their entireties.

The invention relates to the treatment of Amyotrophic lateral sclerosis (ALS), and also to demyelinating neuropathies and neuromyelitis optica (NMO).

Motor neuron diseases (MNDs) are a group of incurable neurological disorders caused by the selective degeneration of motor neurons. Amyotrophic lateral sclerosis (ALS) or Lou Gehrigs Disease is the most representative MND among adults with an incidence rate of 2-3 per 100,000/year (Schmitt et al., 2014). It is characterized by progressive muscle weakness and atrophy, loss of upper and lower motor neurons and death ensuing 3-5 years after diagnosis.

Majority of ALS patients are of sporadic origin with unclear ethiopathology. Several mutations are associated with ALS, in particular in genes encoding superoxide dismutase 1 (SOD-1), TAR DNA binding protein of 43-kDa (TDP-43), fused in sarcoma (FUS) and chromosome 9 open reading frame 72 (C9ORF72). Thus, several transgenic mouse models overexpressing various mutant genes have been developed, and the SOD1 model, overexpressing a mutated form of SOD1 gene, is the most studied in ALS.

There are currently no real satisfactory treatments for ALS. Current clinical practice for patients affected by ALS includes a combination of proactive, adjunctive and symptomatic therapies. So far, no effective therapeutics has been found to fundamentally alter the disease course of ALS beyond riluzole, a putative glutamate release blocker linked to modestly prolonged survival with an average of 2-3 months (Mitsumoto et al., 2014, Lancet Neurol. November; 13(11):1127-38).

As indicated from Wikipedia, Riluzole may have a greater survival benefit for those with a bulbar onset. It also extends the time before a person needs ventilation support. People taking it must be monitored for liver damage (occurring in about 10% of people taking the drug). It is approved by Food and Drug Administration and recommended by the National Institute for Clinical Excellence. Riluzole does not reverse damage already done to motor neurons.

See (http://en.wikipedia.org/wiki/Amyotrophic_lateral_sclerosis#Management)

Other medications may be used to help reduce fatigue, ease muscle cramps, control spasticity, and reduce excess saliva and phlegm. Drugs also are available to help patients with pain, depression, sleep disturbances, dysphagia, and constipation. Baclofen and diazepam are often prescribed to control the spasticity caused by ALS, and trihexyphenidyl or amitriptyline may be prescribed when people with ALS begin having trouble swallowing their saliva.

However, as indicated above, even though these drugs are useful to treat some symptoms ALS, they will not help to stop or revert the course of the disease.

Biotin (or vitamin H) is a ubiquitous water-soluble vitamin which is naturally found in many foods, such as offal, eggs and certain vegetables. In mammals, biotin acts as a cofactor for four metabolism carboxylases involved in several key steps of energy metabolism, including pyruvate carboxylase (neoglucogenesis), 3-methylcrotonyl CoA and propionyl CoA carboxylases (catabolism of certain amino acids which supply the Krebs cycle with intermediate metabolites), and acetyl CoA carboxylase (fatty acid synthesis).

Consequently, the mechanism of action of biotin can bee seen as an enhancer of brain energy (ATP) production.

WO 2011/124571 describes the use of biotin at a high dose (of the order of 100 to 600 mg/day) for the treatment of visual impairments, in particular related to optic atrophy. It should be noted that the visual impairments actually described in this application are symptoms related to a particular leukoencephalopathy, i.e. an involvement of the white matter of the brain. This document neither describes nor suggests that biotin could be used for the treatment of ALS.

WO 2014/016003 describes the use of biotin at a high dose (of the order of 100 to 600 mg/day) for the treatment of multiple sclerosis (MS), stroke and X-linked adrenoleukodystrophy (X-ALD), in particular adrenomyeloneuropathy (AMN). WO 2014/177286 provides evidence that biotin is useful for treatment of AMN.

In the context of the present invention, it is proposed to use biotin, in particular at a high dose, in order to improve the condition of patients suffering from ALS.

The fact that biotin can be useful for ALS treatment and could ultimately limit the evolution of the disease, and even revert some symptoms thereof is particularly novel and surprising, even in view of the results obtained when MS patients are treated with biotin. Indeed, although ALS and MS are neurological diseases that share many traits, their causes, symptoms, and prognoses are very different.

Some of the differences between the two diseases are:

MS may be classified as an autoimmune disease. Autoimmune diseases occur when the immune system mistakenly attacks normal, healthy parts of the body as if they were foreign and dangerous. In the case of MS, the body mistakes myelin-a protective sheath that coats the outside of the nerves for an invader and tries to destroy it. ALS is not an autoimmune disease, and its cause is unknown.

MS targets and attacks myelin in a process called demyelination, hindering the nerves from performing as well as they once did. ALS, on the other hand, attacks the nerves first. In ALS, the demyelination process begins later, after the nerves have begun to die. A magnetic resonance imaging (MRI) scan can detect demyelination. Doctors can use MRI results to distinguish between the two conditions.

According to the National Institute of Neurological Disorders and Stroke, eventually all individuals with ALS will become unable to walk, stand, or move about without help. They also may develop great difficulty swallowing and chewing. Ultimately, ALS is fatal. The outlook isn't as clear with MS. Symptoms of MS may come and go, depending on the type of MS. Patient may experience an attack and then symptoms disappear for days, weeks, even years. The progression of MS differs from person to person. However, it progresses over a much longer period of time than ALS and it's rarely fatal.

In summary, the progression, treatments, and prognoses for ALS and MS are very different.

The invention thus relates to biotin for use thereof in the treatment of amyotrophic lateral sclerosis.

Also subjects of the invention are compositions containing biotin for the use thereof in the treatment of amyotrophic lateral sclerosis, and also the use of biotin for the production or manufacture of a drug intended for the treatment of amyotrophic lateral sclerosis. The teachings of the invention thus make it possible to implement treatment methods comprising the administration of biotin to patients suffering from amyotrophic lateral sclerosis. The invention thus also relates to a method for treating a patient suffering from amyotrophic lateral sclerosis, comprising the step of administering biotin to said patient. Examples of dosage of biotin, and treatment regimen are disclosed below.

Biotin can be used alone or in combination with another compound used for treating amyotrophic lateral sclerosis (or symptoms thereof, as it has been indicated above that there currently is no treatment that lead to improvement of the patient condition), such compound, such as riluzole, baclofen, diazepam trihexyphenidyl or amitriptyline, being administered to bring relief to a patient with amyotrophic lateral sclerosis.

The invention therefore covers a composition containing biotin and also another medicament against amyotrophic lateral sclerosis, for simultaneous, separate or sequential (spread out over time) use in the treatment of amyotrophic lateral sclerosis.

The invention also describes and relates to a method of treating a patient suffering from amyotrophic lateral sclerosis, comprising the steps of providing biotin to said patient, and optionally (but preferably) another drug useful for providing relief to said patients with regards to the symptoms of amyotrophic lateral sclerosis.

Biotin can, in particular, be used to stabilize of the limbs weakness and/or swallowing and or provide some correction to muscle atrophy in lower extremities, in particular assessed by better exercise tolerance during physical therapy.

Treatment with biotin can also lead to increase of the weight of the patient and/or can be used to improve respiratory capacity of the patient.

Biotin may also be used, at high doses, for treatment of other diseases, in particular of demyelinating neuropathies, in particular peripheral neuropathies.

The invention thus also relates to biotin for use thereof in the treatment of a demyelinating neuropathy, in particular a peripheral neuropathy.

Also subjects of the invention are compositions containing biotin for the use thereof in the treatment of a demyelinating neuropathy, in particular a peripheral neuropathy, and also the use of biotin for the production (manufacture) of a drug intended for the treatment of a demyelinating neuropathy, in particular a peripheral neuropathy. The teachings of the invention thus make it possible to implement treatment methods comprising the administration of biotin to patients suffering from a demyelinating neuropathy, in particular a peripheral neuropathy. The invention thus also relates to a method for treating a patient suffering from a demyelinating neuropathy, in particular a peripheral neuropathy, comprising the step of administering biotin to said patient. Examples of dosage of biotin, and treatment regimen are disclosed below.

Biotin can be used alone or in combination with another compound used for treating a demyelinating neuropathy (or symptoms thereof) such compound or treatment being administered to bring relief to a patient with a demyelinating neuropathy.

The invention therefore covers a composition containing biotin and also another medicament against a demyelinating neuropathy, for simultaneous, separate or sequential (spread out over time) use in the treatment of a demyelinating neuropathy.

The invention also describes and relates to a method of treating a patient suffering from a demyelinating neuropathy, comprising the steps of providing biotin to said patient, and optionally (preferably) another drug useful for providing relief to said patients with regards to the symptoms of a demyelinating neuropathy.

Such other compounds, medicament or drugs are more precisely described below.

Such demyelinating neuropathy may be chronic inflammatory demyelinating polyradiculoneuropathy.

In particular, such demyelinating neuropathy may be typical chronic inflammatory demyelinating polyradiculoneuropathy.

Alternatively, such demyelinating neuropathy may be atypical chronic inflammatory demyelinating polyradiculoneuropathy.

Such demyelinating neuropathy may be demyelinating neuropathy associated with immunoglobulin M monoclonal gammopathy and antibodies against myelin-associated glycoprotein (MAG).

Such demyelinating neuropathy may be Charcot Marie Tooth Ia (CMT Ia) disease.

Chronic Inflammatory Demyelinating Polyradiculoneuropathy (CIDP)

Chronic inflammatory demyelinating polyradiculoneuropathy (CIDP) is an acquired paralytic illness affecting peripheral nerves and caused by a demyelinating process.

CIDP is a rare disease. The various epidemiological studies show that prevalence may vary from 1.24/100 000 to 8.9/100 000. Due to the ambiguities of diagnosing CIDP, the true prevalence of the disease may be underestimated or overestimated. The etiology of CIDP is unknown even if rare cases can be associated with different conditions, such as diabetes mellitus, sarcoidosis, disseminated lupus erythematosus, idiopathic monoclonal gammopathy.

Chronic inflammatory demyelinating polyneuropathy (CIDP) is an immune neuropathy. Current diagnostic criteria are based mainly on clinical and neurophysiological parameters that may help distinguish CIDP from other neuropathies, including chronic idiopathic axonal polyneuropathy, diabetic polyneuropathies and amyotrophic lateral sclerosis. The most recent recommendation by the European Federation of Neurological Societies allows for the distinction among definite, probable and possible CIDP diagnoses based on the clinical diagnostic criteria of typical CIDP and atypical CIDP (J Peripher Nery Syst. 2010 March; 15(1):1-9). Typical CIDP is characterized by a chronically progressive, stepwise, or recurrent symmetric proximal and distal weakness and sensory dysfunction of all extremities, developing over at least 2 months; cranial nerves may be affected; and absent or reduced tendon reflexes in all extremities. Atypical CIDP may have normal tendon reflexes in unaffected limbs: predominantly distal (distal acquired demyelinating symmetric, DADS) or asymmetric [multifocal acquired demyelinating sensory and motor neuropathy (MADSAM), Lewis-Sumner syndrome] or focal (e.g., involvement of the brachial or lumbosacral plexus or of one or more peripheral nerves in one upper or lower limb); or pure motor; or pure sensory (including chronic immune sensory polyradiculopathy affecting the central process of the primary sensory neuron) neurological deficits.

The temporal course may be characterized by a subacute onset or acute onset, a relapsing-remitting course or a progressive course. The long term prognosis of CIDP patients is not so good after five years with 39% of patients still requiring immune treatments and 13% with severe disabilities (Kuwabara 2006, J Neurol Neurosurg Psychiatry.

January; 77(1):66-70). The prognosis of CIDP is related to axonal loss secondary to inflammatory demyelination (Hughes et al., 2006, J Peripher Nery Syst. March; 11(1): 30-46).

Various mechanisms may be instrumental in CIDP including presence of auto-antibodies, inflammatory mediators (tumor necrosis factor alpha, interleukin 1, matrix metalloproteinases 2 and 9, complement fractions, chemokines), lymphocyte proliferation, modulation of the Fcγ RII/Fcγ RIII ratio on macrophages. Whatever the involved mechanisms, the consequences include alteration of nerve excitability due to demyelination, decrease of Na+/K+ ATPase pump function, intra-axonal Na+ accumulation associated with energetic failure, leading process to axonal degeneration in inflammatory demyelinating processes (Stys and Waxman, 1994, Muscle Nerve. September; 17(9):969-74; Bechtold and Smith, 2005, J Neurol Sci. June 15; 233(1-2): 27-35).

Corticosteroids, plasma exchange, and intravenous (IV) immunoglobulin (IVIg) have shown efficacy in controlled trials. These compounds may thus be used in combination with biotin. The choice of therapy depends on several factors, including disease severity, concomitant illnesses, adverse-effect profile, potential drug interactions, venous access, age-related risks, and cost of treatment. Corticosteroids is considered as a first line or second line treatment option and have been used to treat CIDP for a long time. It is usually initiated with a dose of 1 mg/kg with a tapering after several months according to clinical response. IVIg is widely used in the treatment of CIDP. Treatment by intravenous immunoglobulins, (IVIgs) can provide significant clinical benefits in more than 60% of CIDP patients (Vermeulen et al., 1993, J Neurol Neurosurg Psychiatry. January; 56(1):36-9; Hahn et al., 1996, Brain. August; 119 (Pt 4):1067-77; Mendell et al., 2001, Neurology. February 27; 56(4):445-9). Clinical improvement often occurs within a few days following IVIg infusions. However, such improvement usually lasts for a few weeks and periodic IVIg infusions are required to maintain therapeutic benefit. Finally, the long term effect of IVIG has not been investigated for more than 6 months (the ICE trial (Merkies et al, Neurology. April 14; 72(15):1337-44)). Moreover, there is no data on the prevention of axonal degeneration with these treatment options.

Demyelinating Neuropathy associated with Immunoglobulin M (IgM) Monoclonal Gammopathy and Antibodies against Myelin-Associated Glycoprotein (MAG)

Polyneuropathy associated with IgM monoclonal gammopathy and antibodies against myelin-associated glycoprotein (MAG) belongs to the group of chronic demyelinating polyneuropathies. It is a chronic progressive disorder that leads to a variable degree of functional impairment and disability.

Most patients have a symmetric sensorimotor polyneuropathy, sensory ataxia, painful paresthesia and upper limb tremor. The disease may progress slowly over many years in some patients, whereas others develop significant disability mostly due to dysesthesia and ataxia; thus, there is a need to develop effective treatments.

A causative role of the IgM M protein in the polyneuropathy is illustrated by the presence of circulating anti MAG antibodies or other antibodies directed at the myelin sheath of peripheral nerves that lead to enlargement of the myelin sheath. Patients present with a striking immunochemical profile, suggesting the possibility of an autoimmune mechanism: monoclonal IgM recognizes a carbohydrate MAG epitope, which is shared with a number of other glycoconjugates involved in cell adhesion, including the Po glycoprotein of myelin, peripheral myelin protein, sulfated sphingolipid, and other related glycolipids. The nerve examination shows widening of myelin lamellae.

There is no consensus about the best treatment strategy, besides the timing of initiation of treatment has not been determined for anti-MAG neuropathy. Immunotherapy and chemotherapy may act through direct suppression or elimination of the B cell clone, or by suppression of the inflammatory cascade. (article endoxan et cortisone). There is insufficient evidence from most pilot studies or randomized controlled trials (RCT) on IgM anti-MAG demyelinating neuropathy to recommend any particular immunotherapy. Rituximab has been considered as promising, but it seems that it didn't really improve the patients condition in a controlled trial (Broglio, and Lauria (2005). Muscle & Nerve, 32(3), 378-379; Léger et al, Neurology. 2013 Jun. 11; 80(24): 2217-2225). However, it could be used together with biotin in the context of the present invention.

Charcot Marie Tooth Ia (CMT Ia) Neuropathy

Charcot-Marie-Tooth disease Type 1A (CMT1A) belongs to the group of inherited, progressive, chronic sensory and motor peripheral neuropathies referred to as Charcot-Marie-Tooth (CMT) disease or as "Hereditary Motor and Sensory Neuropathy" (HMSN). CMT1A accounts for 50% of patients with CMT, with an estimated prevalence of 1 in 5,000. CMT1A is an autosomal dominant disorder caused in the vast majority of cases by a 1.4 megabase-long duplication of chromosome 17p11.2, encompassing the PMP22 gene.

Typical clinical features of CMT1A include weakness of the foot and lower leg and foot deformities (most frequently pes cavus), which appear to be due to weakness of the small intrinsic muscles of the feet. Later in the disease, weakness and muscle atrophy may occur in the hands, resulting in difficulty with fine motor skills. The severity of symptoms is quite variable from one patient to another and even among affected members of the same family.

PMP22 encodes a transmembrane peripheral myelin protein. The duplication of the PMP22 gene results in its overexpression and in abnormal Schwann cell differentiation. The consequences are an homogeneous and diffuse nerve conduction slowing and dysmyelination, eventually leading to axonal loss and muscle wasting.

There is currently no approved treatment for CMT1A. Supportive therapies mainly address disease symptoms such as neuropathic pain, weakness and limb deformities. They include treatment of pain (anti-inflammatory/analgesics, anti-depressants or anti-convulsants for neuropathic pain), physiotherapy (muscle strength training), occupational therapy, orthopaedic devices (including braces and high top shoes) and orthopaedic surgery. However these treatments are not sufficient to limit impairment of motor function and worsening of disability. Ascorbic acid (AA) has shown to promote myelination in vitro and to possibly decrease PMP22 expression. Following this, six clinical trials assessing efficacy and tolerability of 1- or 2-year AA treatment were published, but no clinical benefit was observed in any of these trials. In addition, the results from a double-blind, randomized, placebo-controlled dose ranging phase 2 study of PXT3003 (a low dose combination of three already approved compounds: (RS)-baclofen, naltrexone hydrochloride and D-sorbitol) were published (Attarian et al, Orphanet J Rare Dis. 2014 Dec. 18; 9:199). This trial confirmed the potential good safety and tolerability of PXT3003. The highest dose showed preliminary but consistent evidence of efficacy, with a modest clinical benefit in these adult patients. In particular, biotin may be used to improve walking ability of the patients.

Another demyelinating neuropathy that can be treated by biotin is "acute inflammatory demyelinating neuropathy", better known as Guillain-Barré syndrome, which can damage motor, sensory, and autonomic nerve fibers.

Treatments for this disease include plasmapheresis, filtering antibodies out of the bloodstream, or administering intravenous immunoglobulins (IVIg), to neutralize harmful antibodies and inflammation causing disease, as well as potential use of painkillers as pain is common in people with Guillain-Barré syndrome. Biotin is of particular interest following the acute phase, when rehabilitation is performed on the patient, in order to improve activities of daily living (ADLs). Biotin can, in particular, help recover some functional abilities or speed up such functional recovery. Biotin may thus help revert disabilities observed following the acute phase.

The invention thus also relates to biotin for use thereof in the treatment of neuromyelitis optica.

Neuromyelitis optica (NMO), also known as Devic's disease or Devic's syndrome, is a heterogeneous condition consisting of recurrent and simultaneous inflammation and demyelination of the optic nerve (optic neuritis) and the spinal cord (myelitis).

Currently at least two different causes are proposed based on the presence of autoantibodies against AQP4. AQP4+ NMO is currently considered an autoimmune disease (autoimmune astrocytopathy, or autoimmune astrocytic channelopathy) in which a person's own immune system attacks the astrocytes of the optic nerves and spinal cord. The cause of the AQP4− variants is unknown.

Although inflammation may also affect the brain, the lesions are different from those observed in a related condition, multiple sclerosis. Spinal cord lesions lead to varying degrees of weakness or paralysis in the legs or arms, loss of sensation (including blindness), and/or bladder and bowel dysfunction.

Devic's disease is a rare disorder which resembles multiple sclerosis (MS) in several ways but is not a multiple sclerosis variant (Barnett and Sutton, 2012, Curr Opin Neurol. June; 25(3):215-20), and requires a different course of treatment for optimal results.

The main symptoms of Devic's disease are loss of vision and spinal cord function. Optic neuritis may manifest as visual impairment with decreased visual acuity, although visual field defects, or loss of color vision may occur in isolation or prior to formal loss of acuity. Spinal cord dysfunction can lead to muscle weakness, reduced sensation, or loss of bladder and bowel control. The typical patient has an acute and severe spastic weakness of the legs (paraparesis) or all four limbs (quadriparesis) with sensory signs, often accompanied by loss of bladder control.

The Mayo Clinic proposed a revised set of criteria for diagnosis of Devic's disease in 2006. The new guidelines require two absolute criteria plus at least two of three supportive criteria.

Absolute Criteria: Optic Neuritis and Acute Myelitis

Supportive criteria: Brain MRI not meeting criteria for MS at disease onset, Spinal cord MRI with contiguous T2-weighted signal abnormality extending over three or more vertebral segments, indicating a relatively large lesion in the spinal cord, NMO-IgG seropositive status (The NMO-IgG test checks the existence of antibodies against the aquaporin 4 antigen).

Currently, there is no cure for Devic's disease, but symptoms can be treated. Some patients recover, but many are left with impairment of vision and limbs, which can be severe. Attacks are treated with short courses of high dosage intravenous corticosteroids such as methylprednisolone IV. Plasmapheresis can be an effective treatment when attacks progress or do not respond to corticosteroid treatment.

No controlled trials have established the effectiveness of treatments for the prevention of attacks. Many clinicians agree that long term immunosuppression is required to reduce the frequency and severity of attacks, while others argue the exact opposite. Commonly used immunosuppressant treatments include azathioprine (Imuran) plus prednisone, mycophenolate mofetil plus prednisone, rituximab, mitoxantrone, intravenous immunoglobulin (IVIG), and cyclophosphamide. The monoclonal antibody rituximab is under study. In 2007, Devic's disease was reported to be responsive to glatiramer acetate and to low-dose corticosteroids. These treatments can be used in combination with biotin.

Biotin can be used in particular to improve visual acuity of the patients, and/or strength of the patient's limbs. Biotin can thus be used to improve walking abliblity of the patients.

Also subjects of the invention are compositions containing biotin for the use thereof in the treatment of neuromyelitis optica, and also the use of biotin for the production of a drug intended for the treatment of neuromyelitis optica. The teachings of the invention thus make it possible to implement treatment methods comprising the administration of biotin to patients suffering from neuromyelitis optica. The invention thus also relates to a method for treating a patient suffering from neuromyelitis optica, comprising the step of administering biotin to said patient. Examples of dosage of biotin, and treatment regimen are disclosed below.

Biotin can be used alone or in combination with another compound used for treating neuromyelitis optica (or symptoms thereof), such compound or treatment being administered to bring relief to a patient with neuromyelitis optica.

The invention therefore covers a composition containing biotin and also another medicament against neuromyelitis optica, for simultaneous, separate or sequential (spread out over time) use in the treatment of neuromyelitis optica.

The invention also describes and relates to a method of treating a patient suffering from neuromyelitis optica, comprising the steps of providing biotin to said patient, and optionally another drug useful for providing relief to said patients with regards to the symptoms of said neuromyelitis optica.

Such other compounds, medicament or drugs are more precisely described above or below.

For treatment of the above diseases, biotin may be used as follows.

The biotin is preferentially administered at a therapeutically effective amount, which is generally a high dose, i.e. at a dose of at least or about or exactly 50 mg per day. Even if a maximum dose is not really envisaged, the latter should not generally exceed 500 mg, 600 mg or 700 mg per day. This makes it possible to observe improvement in the condition of the patient, and/or stop or decrease of the worsening of the condition of the patient.

In that way, the pratician may determine the dose according to the weight of the patient. In particular, a dose at least equal to 1 mg/kg/day, preferably 3 mg/kg/day, preferably 5 mg/kg/day, or at least equal to 7.5 mg/kg/day, or even around 10 mg/kg/day, is administered to the patient.

Between 50 and 700 mg of biotin per day are thus administered to the patients, generally between 50 and 500 mg per day, or between 50 and 600 mg per day, more preferably between 100 and 300 mg per day, generally around 300 mg per day. One can thus administered at least or about or exactly 50 mg par day, more preferably at least or about or exactly 100 mg per day, or at least or about or exactly 150 mg per day, or even at least or about or exactly 200 or at least or about or exactly 250 mg per day, or at least or about or exactly 300 mg per day.

In one particular embodiment which is preferred (in particular for problems of ease of use by the patient), the biotin is in a form suitable for oral administration. This therefore involves a composition for oral administration, which will contain at least or about or exactly 20 mg, preferably at least or about or exactly 40 mg of biotin, or even at least or about or exactly 50 mg, at least 7 or about or exactly 5 mg, at least or about or exactly 100 mg, at least or about or exactly 150 mg or at least or about or exactly 250 mg of biotin. This composition is preferentially for pharmaceutical use, and is therefore a medicine. It is understood that each unit dose of this composition contains at least or about or exactly 20 mg, preferably at least or about or exactly 40 mg, or even at least or about or exactly 50 mg, at least or about or exactly 100 mg, at least or about or exactly 150 mg or at least or about or exactly 250 mg of biotin, as active ingredient.

The total dose of biotin may be administered once a day, of through multiple takes. In particular, biotin may be taken through two or three takes a day. It is preferred when biotin is taken around meal times, and when the amount of biotin is substantially the same for each take.

It is to be noted that the diseases herein described are chronic disease, with worsening over time. It is thus preferable that treatment with biotin is performed in the long run, in order to be the most effective and to stabilize any improvement that it will bring. Consequently, it is preferred when said treatment with biotin has a duration of at least 3 months. It is even preferred when said treatment with biotin has a duration of at least 6 months. As indicated, such treatment may be prolonged as long as possible in order to increase the improvement brought by biotin, and stabilize the therapeutic effects. In particular, said treatment with biotin has a duration of at least one year. There is no envisaged term for the treatment and it is expected that the patient will take biotin as long as it is needed and will improve or stabilize the condition of the patient.

In one particular embodiment, this composition for oral administration contains biotin as sole active ingredient, and also excipients, without any other active ingredient.

An excipient should be understood to mean any compound forming part of the formulation which is intended to act as a simple support, i.e. which is not intended to have a biological activity.

This composition can be in any form known in the art. In particular, it is in the form of gel capsules, tablets (optionally film-coated), pills or lozenges. In another embodiment, it is in the form of a syrup. Said syrup contains an amount such that it contains at least or about or exactly 20 mg, preferably at least or about or exactly 40 mg, or even at least or about or exactly 50 mg, at least or about or exactly 75 mg or at least or about or exactly 100 mg of biotin per unit dose. The concentration of biotin in this syrup depends on the unit dose that it is desired to give to the patient.

Excipients which can be used by those skilled in the art are well known in the art. Talc (E553b), microcrystalline cellulose, lactose, mannose, starch (in particular corn starch), magnesium stearate (E572) and stearic acid (E570) can thus be chosen. This list is not exhaustive.

When this composition is prepared in the form of gel capsules, a preferred excipient is microcrystalline cellulose.

When the composition is in the form of a film-coated tablet, said film-coating may be formed from any substance known in the art, such as hypromellose (E464), ethylcellulose, macrogol, talc (E553b) titanium dioxide (E171) or iron oxide (E172).

The active ingredient may also be colored (by any acceptable coloring, such as cochineal), thereby making it possible to verify that the biotin is well dispersed in the excipient.

A slow release (or slow sustained) form may also be envisaged given the fact that plasma half life of biotin is short (about 2 hours).

Said slow release compositions are known in the art and described in particular in WO 2011/077239. In particular, said slow release compositions may comprise a slow release matrix comprising biotin alone or with one or more active ingredient(s).

In a specific embodiment, the slow release composition comprises a matrix allowing immediate release, wherein said matrix comprises biotin alone or with one or more other active ingredient(s) and the slow release is achieved by a release modifying matrix or coating.

Thus, the slow release composition may provide immediate release and differed (slow) release of biotin.

In a specific embodiment slow release may be achieved through an osmotically driven release system.

In another embodiment, the slow release composition comprises a core comprising biotin, optionally one or more active ingredient(s), and optionally pharmaceutical excipient(s) and one or more outer layers, wherein the outer layers comprises one or more slow release agent(s).

In another aspect, the biotin may be in the form which allows administration by injection: this then involves an injectable composition containing at least or about or exactly 20 mg, preferably at least or about or exactly 40 mg, or even at least or about or exactly 50 mg, at least or about or exactly 75 mg, at least or about or exactly 100 mg, at least or about or exactly 150 mg or at least or about or exactly 250 mg of biotin per unit dose.

This injectable composition may be in the form of a vial containing the biotin, and also acceptable excipients. The concentration of biotin is adjusted according to the envisaged volume of the vial. Certain excipients which improve biotin solubility can be used.

The excipients that can be used for the production of injectable compositions are well known in the art. Mention may in particular be made of sodium dihydrogen phosphate, sodium bicarbonate (E550i), methyl para-hydroxybenzoate (E218) and propyl para-hydroxybenzoate (E216), which can be used together in proportions that those skilled in the art are capable of determining. The water used is water for injection. The injection is preferably carried out intramuscularly. It can also be carried out intravenously.

EXAMPLES

Example 1—Treatment of ALS

A patient suffering from ALS has been treated with high doses biotin (100 mg three times a day) and showed some stabilization of its disability.

This 47-old man started to exhibit symptoms of ALS in February 2013 with speech difficulty—slow and slurred speech. The speech difficult worsened for several months and then the patient started to exhibit lower limb weakness in summer 2013 together with some low back pain occasionally radiating to the legs. EMG study disclosed diffuse neurogenic changes with fibrillation potentials. Fasciculations were recorded. A right quadriceps biopsy (November 2013) concluded in "neurogenic atrophy" per report. CK (creatine kinase) has been intermittently elevated around 350-500. Other outside test results were negative: Lyme serology, HIV antibodies (abs), ENA, AChR abs, MuSK abs, GM1 abs, gene test from myotonic dystrophy type 2: negative. Asialoganglioside GM1: just above upper limit of normal. PET CT: negative per report. Brain MRI with contrast: negative per report. MRI L-spine: negative per report. Gene test for Kennedy disease was negative.

The patient continued to worsen and he developed respiratory distress necessitating the tracheostomy and mechanical ventilation over the year 2015. He had, in addition to his weakness, lots of fasciculation in his 4 limbs that disappeared at this stage. When examined in September 2015, he had 2/5 motor power in his arms (weaker on the right side) and 3+/5 in his forearms and hands. In his lower extremities: Quadriceps 2/5, Iliopsoas 0/5, Tibialis anterior and Gastrocnemius 2/5 to 1/5 bilaterally. His reflexes were hyperactive in his upper extremities but absent in the lower extremities with negative Babinski sign.

Treatment with biotin 100 mg three times a day was started the 11 Sep. 2015. At that time other medications encompassed Glutathion, Azithromycin, Laroscorbine, Euthyrox, Mucosolvan, Probiotics, Tryptizol (amitriptyline) 40 mg, Zoloft 50 mg, Doxicycline 200 mg, Zyprexa 7.5 mg, Omega 3, Vitamin E 500 mg and riluzole 50 mg. All these medications were introduced at least 6 months before. The neurologist, the family and the patient noticed stabilization of the limbs weakness and swallowing after 3 and 6 months with some subtle positive improvement: there was some improvement of muscle atrophy in lower extremities with better exercise tolerance during physical therapy. The weight of the patient slightly increased. The respiratory capacity seemed to improve slightly: the patient could switch off the medical ventilator for one hour a day after 3 months of treatment and then for 4 hours a day after 6 months of treatment. Noticeably, the patients was dependent on the ventilator 24 hours a day at the beginning of treatment thus the progressive decrease in the need for mechanical ventilation can be considered as a significant improvement of respiratory muscles strength.

Example 2: Animal Studies for ALS

The transgenic SOD1(G93A) mice is the model of choice to perform such exploratory study as:
 Mice develop a disease similar to ALS (weight loss, progressive paralysis).
 The disease start sooner (110 days vs 8.5/9 months) and develop faster (death in 5.5 months vs 14 months) than in other SOD models.
 Cohorts are very homogeneous in terms of disease progression.
 Proposed Proof-of-Concept experiment:
The effect of biotin is evaluated in SOD1(G93A) mice regarding clinical efficacy in terms of improved muscular strength and body weight gain.
 "Clinical" evaluation:
 10 transgenic SOD(G93A) mice
 2 groups of 5 mice: untreated and biotin-treated (custom diet)
 The dose used will be around 30 mg/kg/day which is equivalent to a human dose of 5 to 10 mg/kg/day
 Biotin will be mixed in dry food
 "Clinical" examination: once or twice a week at first, then once a day
  Weight
  Grip test (muscular strength)
 Treatment start: at the weight pic (when mice are aged of about 110 days)
 At around 150 days, non-treated mice generally present a 10% body weight loss and a 35% loss muscular strength
 Treatment is continued until death of the animals (around 170 days for non-treated mice), in order to evaluate the effect on survival
 Histopathological analyses are performed (Nissl staining to evaluate the number of motoneurons, astrogliosis, microgliosis, lumbar spinal cord)

Consequently, this example makes it possible to evaluate the effect of high-dose biotin treatment in terms of clinical score improvement and motor neuron death reduction.

Such transgenic mice are commercially available (in particular from Jackson Laboratories http://jaxmice.jax.org/strain/002726.html).

Example 3: Use of Biotin for Treatment of Chronic Inflammatory Demyelinating Polyneuropathy A clinical trial can be set up for determining the efficacy and safety on motor and sensory conduction of biotin at high doses, in patients suffering from demyelinating polyneuropathies on patients with:
 chronic inflammatory demyelinating polyneuropathy on both clinical and neurophysiological grounds
 proven genetic diagnosis of Charcot-Marie-Tooth 1A
 anti-myelin-associated glycoprotein polyneuropathy.

The inclusion parameter include electrophysiological parameters worsening for the past 3 years.

A primary endpoint is a change from baseline to week 48 in at least two out of the four criteria of demyelination:
 motor nerve conduction velocity,
 distal latency,
 F wave latency,
 length of motor nerve potential, 8 nerves are assessed for those 4 parameters. Change is considered significant when the last value is 10% improved compared to the baseline value for 2 out of the 4 parameters in at least 3 nerves out of 8 investigated nerves.

The secondary endpoints are changes from baseline to week 48 in ONLS (Overall Neuropathy Limitations Scale), MRC score, INCAT scale, Posturometry, 10-meter walk time, 6-min walk test, Min-max absolute refractory period, Refractoriness, Supernormality, Strength-duration time constant, Rheobase (see Table 1).

The secondary endpoints will be evaluated on changes from baseline to week 48.

Biotin Capsules

The investigational drug consist in capsules of 100 mg biotin and excipients (lactose, magnesium stearate, croscarmellose sodium, Silica)

Dose Regimen

The dose regimen is 1 capsule three times a day (one in the morning, one at noon and one in the evening) (300 mg/day).

Example 4: Use of Biotin for Treating Charcot Marie Tooth Disease

Two patients with demyelinating Charcot Marie Tooth (CMT) disease were treated with biotin 300 mg/day.

A 36 year old patient with CMT1a was treated with high doses of biotin (100 mg three times a day). No other treatment was introduced. The patient was followed clinically using a 6 minutes walking test. After 9 months of treatment the maximum walking distance was improved by 100 meters.

A 31 year-old man with CMT1E (a rare form of demyelinating CMT with hearing loss) was treated with high doses biotin (100 mg three times a day). No other drug was introduced. The 6 minutes walk test was at 396 meters at treatment's onset.

After 3 months, the 6 minutes walk test was improved at 515 meters.

After 9 months, the 6 minutes walk test remained improved at 490 meters.

After 12 months, the 6 minutes walk test remained improved at 480 meters.

After 18 months, the 6 minutes walk test remained improved at 483 meters.

After 24 months, the 6 minutes walk test further improved at 580 meters.

Results of the 6 minutes walk test in this patient clearly demonstrated some improvement compared to the pre-treatment value.

Example 5: Use of Biotin for Treatment of Other Diseases

Biotin can be used for treatment of neuromyelitis optica, using the same kind of regimen as disclosed in Examples 1 and 4.

Endpoint would be partial recovery and improvement of vision or of motor strength. Three patients will be treated and assessed every 6 months with measures of visual acuity (VA) and clinical examination including motor strength testing. Results will be considered positive in case of improvement of VA of at least 5 letters associated with any improvement of motor strength.

Results:

Patient 1: this 46 year-old man was diagnosed with Neuromyelitis optica. First episode of right optic neuritis occurred in 2006. This was followed by an attack of tetraplegia in 2009 with positive anti-NMO antibodies. At the time of biotin treatment's onset, the neurological examination showed: visual acuity at 7/10 left and "count the fingers" on right; muscle weakness on right upper limb at 1/5; weakness of lower extremities at 3/5 to 4/5. The patient could not walk. Treatment with biotin (100 mg three times a day) was started. After three months the patient noticed some improvement of right hand movements; this improvement was confirmed after 9 months and the patient and neurologist noticed better strength in the right lower limb. After 24 months of treatment, the patient was reported to walk with two aids and the help of the physical therapist. Visual acuity on the right was slightly improved to 0.25/10. The treatment was very well tolerated.

Patient 2: this 41 year old woman was diagnosed with Neuromyelitis optica in March 2013 with several episodes of optic neuritis since 1994. Treatment with biotin (100 mg three times a day) was introduced. At that time the patient was treated with monthly perfusions of cyclophosphamide. Visual acuity was 0/10 right and 9/10 left. After 4 months of treatment with biotin, visual acuity was 1/10 right and 6/10 left. After 18 months of treatment, visual acuity was 2/10 right and 8/10 left. It was concluded that treatment with biotin improved the right visual acuity.

The invention claimed is:

1. A method for the treatment of a peripheral demyelinating neuropathy, comprising administering to a patient in need thereof a composition comprising an amount of biotin sufficient to treat said demyelinating neuropathy, wherein said demyelinating neuropathy is Charcot Marie Tooth 1a disease or Guillain-Barre syndrome.

2. The method of claim 1, wherein a daily amount of biotin administered to the patient is comprised between 50 and 700 mg.

3. The method of claim 1, wherein a daily amount of biotin administered to the patient is at least 100 mg.

4. The method of claim 1, wherein a daily amount of biotin administered to the patient is at least 150 mg.

5. The method of claim 1, wherein a daily amount of biotin administered to the patient is comprised between 100 mg and 300 mg.

6. The method of claim 1, wherein the composition is in a form suitable for oral administration.

7. The method of claim 1, wherein the composition is in the form of gel capsules, tablets, lozenges or pills.

8. The method of claim 1, wherein the composition comprises biotin and excipients, without any other active ingredient.

9. The method of claim 8, wherein the excipients are chosen from the group consisting of talc, microcrystalline cellulose, lactose and mannose.

10. The method of claim 1, wherein the composition is a form suitable for injectable administration.

11. The method of claim 1, wherein the composition is in the form of a slow release composition.

12. The method of claim 1, wherein said treatment with biotin has a duration of at least 3 months.

13. The method of claim 1, wherein said treatment with biotin has a duration of at least 6 months.

14. The method of claim 1, wherein said treatment with biotin has a duration of at least one year.

* * * * *